United States Patent
Basler

(10) Patent No.: US 8,721,237 B2
(45) Date of Patent: May 13, 2014

(54) DEVICE FOR FABRICATING DENTAL PROSTHETICS AND METHOD

(75) Inventor: Franz Basler, Laudenbach (DE)

(73) Assignee: Sirona Dental Systems GmbH, Bensheim (DE)

( * ) Notice: Subject to any disclaimer, the term of this patent is extended or adjusted under 35 U.S.C. 154(b) by 164 days.

(21) Appl. No.: 13/229,391

(22) Filed: Sep. 9, 2011

(65) Prior Publication Data

US 2012/0087757 A1   Apr. 12, 2012

Related U.S. Application Data

(63) Continuation of application No. PCT/EP2010/053006, filed on Mar. 10, 2010.

(30) Foreign Application Priority Data

Mar. 10, 2009   (DE) .......................... 10 2009 001 428

(51) Int. Cl.
*B23C 3/00*   (2006.01)
*B23C 1/04*   (2006.01)

(52) U.S. Cl.
USPC ........... 409/132; 409/165; 409/166; 409/192; 433/51; 433/223; 408/42; 408/89

(58) Field of Classification Search
USPC .......... 409/131–132, 192, 165–168; 433/223, 433/51; 408/42–45, 69–71, 89–90
See application file for complete search history.

(56) References Cited

U.S. PATENT DOCUMENTS

| | | | | |
|---|---|---|---|---|
| 1,336,800 A | * | 4/1920 | Vincent | 29/888.06 |
| 2,297,551 A | * | 9/1942 | Greve | 409/199 |
| 2,651,975 A | * | 9/1953 | Soloff | 409/184 |
| 2,681,596 A | * | 6/1954 | Klomp | 409/165 |
| 3,187,635 A | * | 6/1965 | Koss | 409/192 |
| 3,548,712 A | * | 12/1970 | Dzus et al. | 409/158 |
| 3,746,459 A | * | 7/1973 | Kindelan | 408/37 |
| 4,625,377 A | * | 12/1986 | Kavthekar | 29/898.043 |
| 6,394,880 B1 | * | 5/2002 | Basler et al. | 451/28 |
| 6,953,383 B2 | * | 10/2005 | Rothenberger | 451/11 |
| 7,044,690 B1 | * | 5/2006 | Charvat | 408/1 R |
| 7,403,830 B2 | | 7/2008 | Weber et al. | 700/98 |
| 2004/0089962 A1 | * | 5/2004 | Valery et al. | 264/16 |
| 2007/0243503 A1 | | 10/2007 | Gagnon et al. | |
| 2009/0290948 A1 | | 11/2009 | Basler | 409/135 |

FOREIGN PATENT DOCUMENTS

| | | |
|---|---|---|
| DE | 37 16 413 A1 | 12/1988 |
| DE | 39 40 797 A1 | 6/1991 |
| DE | 199 28 002 C1 | 10/2000 |

(Continued)

OTHER PUBLICATIONS

International Search Report dated Jul. 14, 2010 (4 pages).

*Primary Examiner* — Daniel Howell
(74) *Attorney, Agent, or Firm* — Fitzpatrick, Cella, Harper & Scinto

(57) ABSTRACT

A machining device for a workpiece wherein a first feed axis extends through a workpiece holder, a first machining tool is disposed on a first side of the feed axis, and a second machining tool is disposed on a side of the feed axis opposing the first side. Between a first feed axis and perpendicular to a second feed axis, at least one machining tools has a predetermined fixed angular offset.

13 Claims, 5 Drawing Sheets

(56) References Cited

FOREIGN PATENT DOCUMENTS

| | | |
|---|---|---|
| DE | 10 2005 016 245 A1 | 10/2006 |
| EP | 0 455 852 B1 | 11/1991 |
| EP | 455853 B1 * | 4/1995 |
| JP | 02243218 A * | 9/1990 |

* cited by examiner

DEVICE FOR FABRICATING DENTAL PROSTHETICS AND METHOD

CROSS REFERENCE TO RELATED APPLICATIONS

This application is a continuation of International Application No. PCT/EP2010/053006 filed on Mar. 10, 2010, and claims the benefit of priority of German Application No. 102009001428.4 filed on Mar. 10, 2009. The entire disclosures of these earlier applications are incorporated by reference as set forth fully herein.

TECHNICAL FIELD

The invention relates to a machining device for a workpiece, more particularly for the fabrication of dental prosthetic items or models thereof, comprising a workpiece holder for the workpiece and a first and a second machining tool, the workpiece holder on the one hand and the first and second machining tools on the other being capable of being moved relatively to each other along a first feed axis extending through the workpiece holder. The first machining tool is disposed on a first side of the feed axis and the second machining tool is disposed on a side of the feed axis that opposes the first side, and the first and second machining tools are capable of being moved relatively to the workpiece along a second feed axis extending through the machining tool. The workpiece is rotatable through at least 180° about the first feed axis.

A further object of the invention is a method for the fabrication of dental prosthetic items or models thereof.

DESCRIPTION OF THE RELATED ART

EP 0 455 853 B1 discloses a grinding machine for dental materials, in which there is a vertically fixed relationship between the tool axes and the workpiece axis. One of two tools disposed in a tool-carrier head can be positioned at an acute angle of 45° relative to the horizontal for the purpose of machining the occlusal surface.

Rotation of the workpiece axis about the feed axis is disclosed in DE 199 28 002 C1. But this permits the production of undercuts in the buccolingual direction only.

This suffers from the drawback that no undercuts can be produced in the mesiodistal direction without the use of a large blank for the purpose.

Since a restoration does not necessarily have a linear insertion direction, i.e. the direction of fitting may change during fitting of a restoration to the prepared tooth, it is desirable to have the possibility of producing undercuts in the mesiodistal direction in order to achieve an accurately fitted dental prosthesis.

SUMMARY OF THE INVENTION

The above object is achieved by the invention as defined in Claim 1 and by the method as defined in Claim 5.

The basic idea of the invention is to tilt the workpiece axis and the tool axis, which actually extend at right angles to each other, by a few degrees. The alteration of the disposition of the workpiece axis relative to the tool axes precisely meets the requirements of improved use of the machining device without adding an additional degree of freedom to the device with the associated deleterious effects on the cost and stability of the device and on the amount of control means required. In place of a complete fifth degree of freedom, provision is thus made for only a slight tilt, for which purpose 5° may be regarded as being sufficient.

Advantageous developments are described in the subclaims.

BRIEF DESCRIPTION OF THE DRAWINGS

The method of the invention is described with reference to the drawings, in which.

DESCRIPTION OF THE EXEMPLARY EMBODIMENTS OF THE INVENTION

Figure 1:
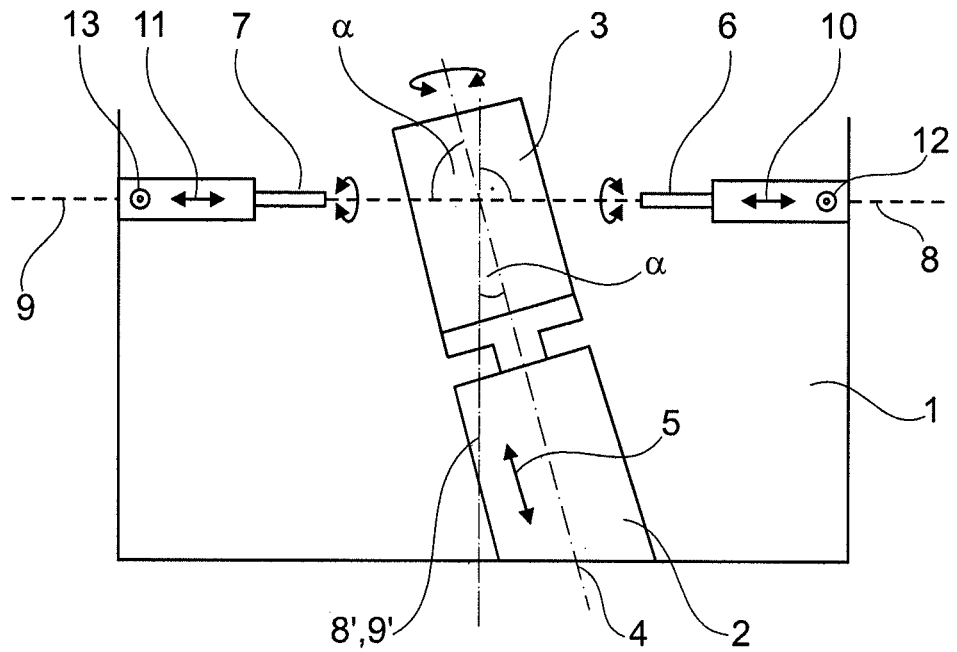
FIG. 1 shows part of a machining device for a workpiece, more particularly for the fabrication of dental prosthetic items or models thereof.

FIG. 1 shows part of a machining device for a workpiece, more particularly for the fabrication of dental prosthetic items or models thereof, namely a machining chamber 1. A workpiece holder 2, which is intended for a workpiece 3 and can be moved forward in the direction of the arrow 5 into the machining chamber 1 along a feed axis 4 and in the reverse direction, protrudes into the machining chamber 1.

A first and a second machining tool 6, 7 are also disposed in the machining chamber 1, the first machining tool 6 being disposed on a first side of the feed axis 4 of the workpiece holder 2 and the second machining tool 7 being disposed on a side of the feed axis 4 of the workpiece holder 2 that is located opposite the first side.

The first and second machining tools 6, 7 are each capable of being moved relatively to the workpiece 3 along a feed axis 8, 9 defined by the machining tools 6, 7 respectively. The machining tools are moved both toward the workpiece 3 and away from the same, as denoted by the arrows 10, 11, and in a direction extending out of and into the plane of the drawing, as denoted by the symbol for an arrowhead 12, 13. The feed axes 8, 9, and 12, 13 can be located in a common plane, as shown in the figure. But the planes can also be located at a distance from each other, for example, when the machining tool 7 is intended to engage the workpiece 3 at a different level from that engaged by the machining tool 6.

In general, the tool holder 2 for the workpiece 3 on the one hand and the first and second machining tools 6, 7 on the other are capable of being moved relatively to each other along a first feed axis 4 defined by the workpiece holder 2 so that the workpiece could also be moved out of the plane of the drawing in place of the movement of the machining tools shown.

There is an angular offset α of not more than 15 degrees and of at least two degrees and preferably of 5° between the feed axis 4 of the workpiece holder 2 and the perpendicular 8', 9' to the feed axis 8, 9 of at least one of the two machining tools 6, 7. As a result, the tool holder 2 is in an inclined position relative to the machining tools 6, 7.

Figure 2:
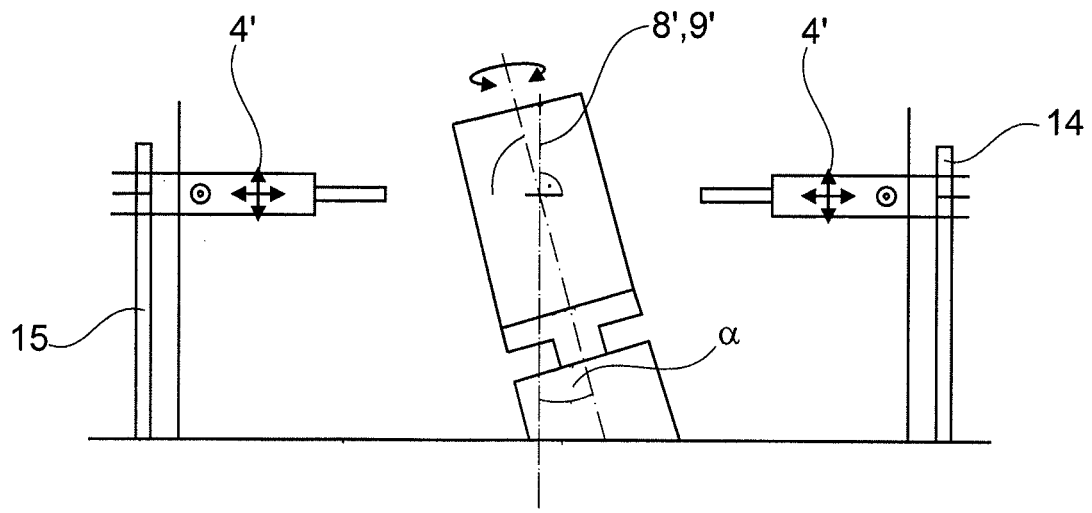
FIG. 2 shows an alternative embodiment to that shown in FIG. 1.

FIG. 2 shows that displacement of the machining tools 6, 7 along the first feed axis 4' is also possible in place of the feed of the workpiece holder 2 that is now stationary and is inclined by the angle alpha relative to the perpendicular 8', 9' to the second feed axis 8, 9. For this purpose, the machining tools 6, 7 can be disposed on a guide 14, 15 so as to be capable of being moved along the first feed axis 4'.

Figure 3:
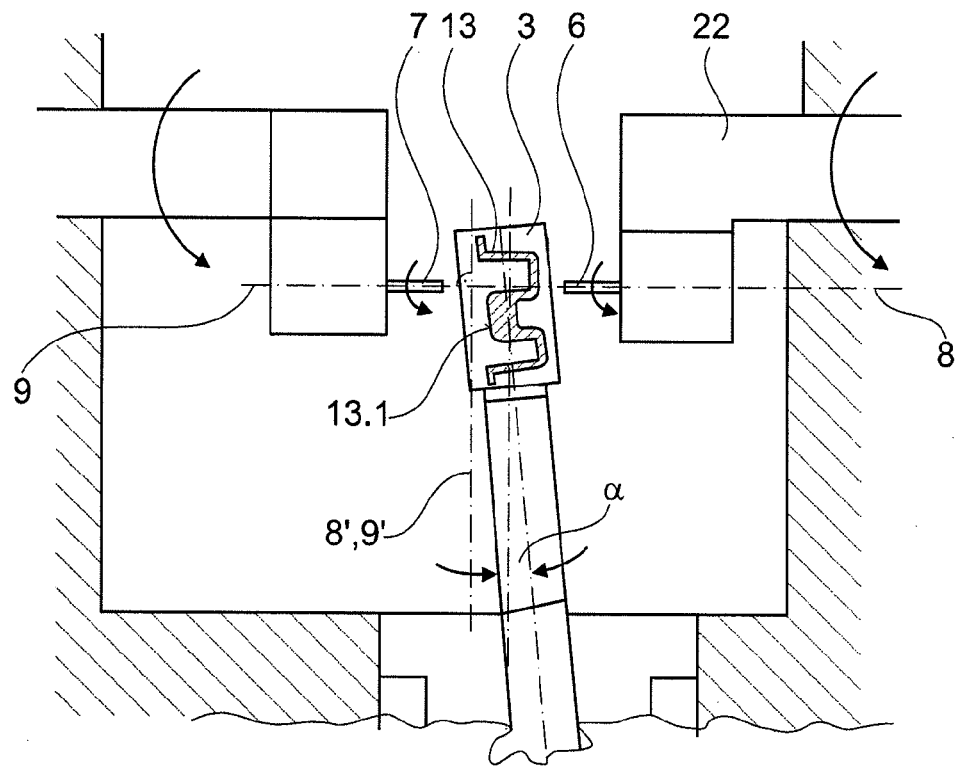
FIG. 3 illustrates the operation of machining a workpiece in a first position.
Figure 4:
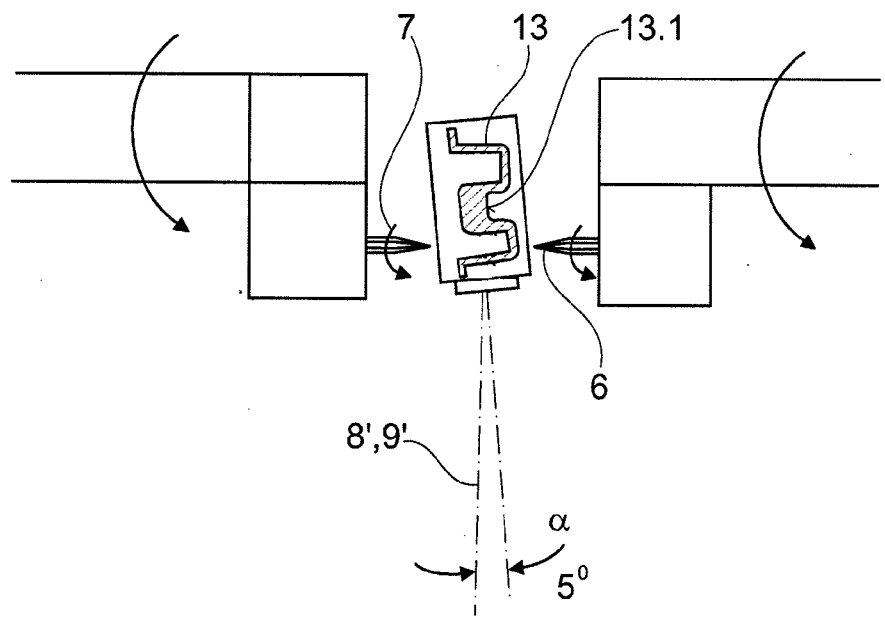
FIG. 4 illustrates the operation of machining the workpiece shown in FIG. 3 in a second position.

FIGS. 3 and 4 illustrate the production of undercuts in the mesiodistal direction with reference to a framework 13 to be carved from the workpiece 3, starting from the situation in which a machining device is set up as shown in FIG. 1. The tools 6, 7 capable of rotating about their own axes, as denoted by the small arrows, can be pivoted out of the plane of the drawing and back into the same, as denoted by the large arrows.

Figure 3A:
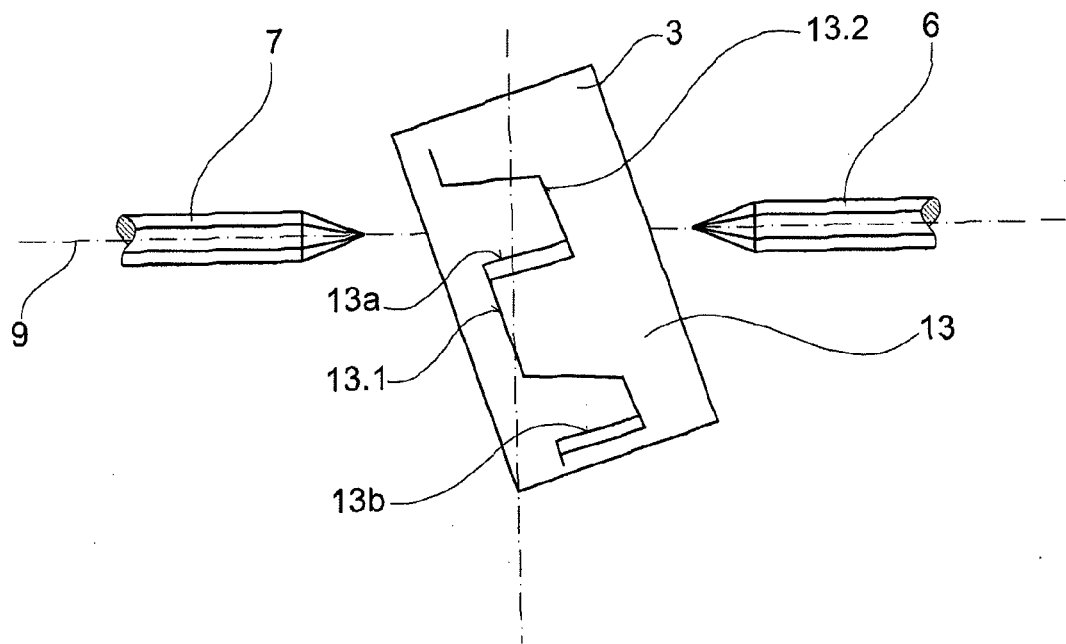

In the first position shown in FIG. 3, the cervical side 13.1 of the workpiece 3 that is tilted in the counterclockwise direction relative to the perpendicular 8', 9' can be machined by means of the machining tool 7, and undercuts relative to the tool axis 8, 9 can be produced within an angular range corresponding to the angle of tilt alpha. FIG. 3A shows this in detail. The faces 13a, 13b of the framework 13, which can be produced only in this position, are machined on the workpiece 3 by means of the machining tool 7 guided along the feed axis 9 from the cervical side 13.1. The opposite side 13.2 of the framework 13, which is an external side, can be machined entirely by means of the machining tool 6.

Figure 4A:
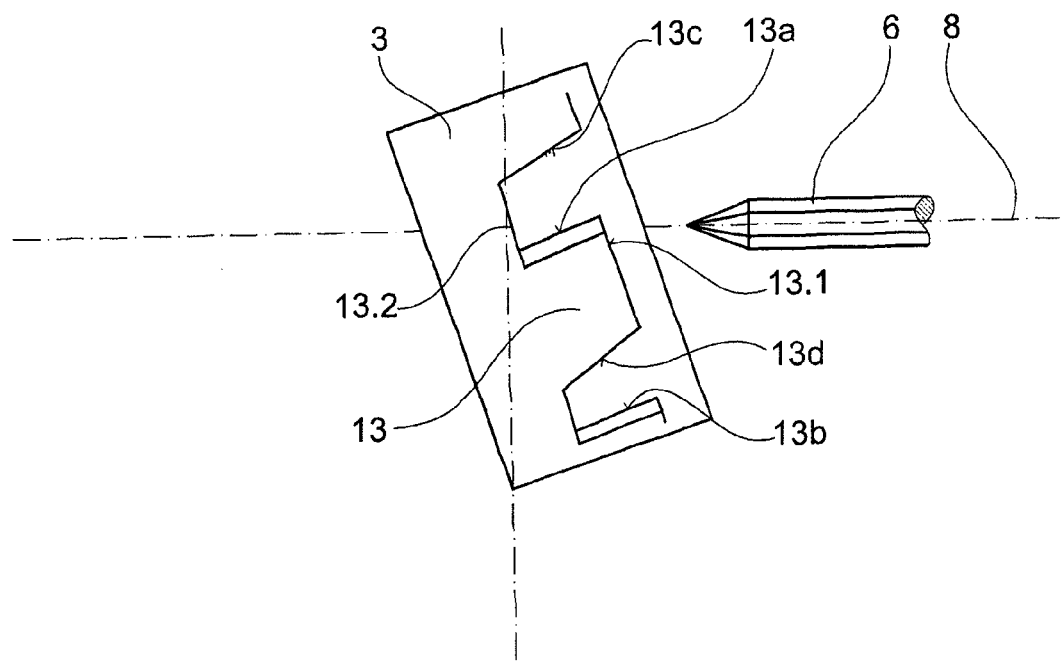

In a second step shown in FIG. 4, the workpiece 3 is moved to the second position, for which purpose the workpiece 3 is preferably rotated through 180°. In this position, the internal contour of the workpiece 3 that is rotated in the clockwise direction relative to the perpendicular 8', 9' is machined by means of the tool 6. FIG. 4A shows this in detail. The faces 13c, 13d of the framework 13, which can be produced only in this position, are machined on the workpiece 3 by means of the machining tool 6 guided along the feed axis 8 from the cervical side 13.1. The faces 13a, 13b cannot be machined further, since they represent an undercut in this position. The opposite side 13.2 of the frame 13, which is an external side, need not be machined further, but it could be completed by means of the machining tool 7, if necessary.

Depending on requirements, the decision can be made when setting up the machining schedule as to whether the workpiece 3 be machined concurrently by means of two machining tools 6, 7 in position 1 or 2 or whether the machining of one side of the workpiece 3 be carried out in two successive procedures in the positions 1 and 2 using two machining tools 6, 7.

Machining of the occlusal side is hardly affected by the tilt of the axes, since this external surface can be readily reached by the tool and since there are usually no undercuts and the opening angles of the surface structures such as fissures are sufficiently large. However, the internal surfaces are closed on one side and naturally cannot be machined from the closed side.

Figure 5A:
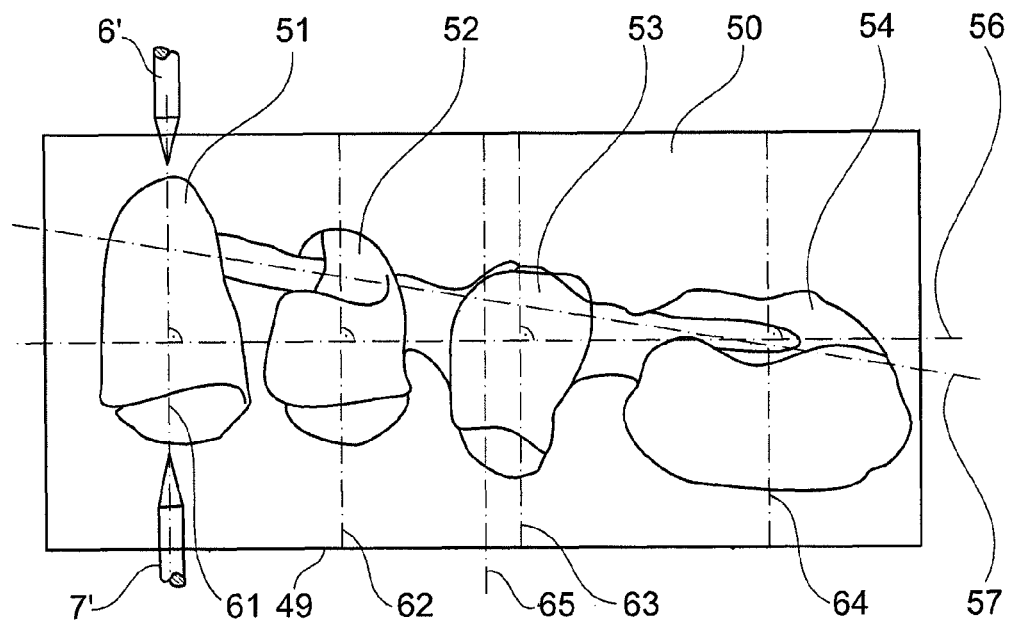
FIG. 5A shows the layout of a dental prosthetic item to be produced from a blank according to the prior art.
Figure 5B:
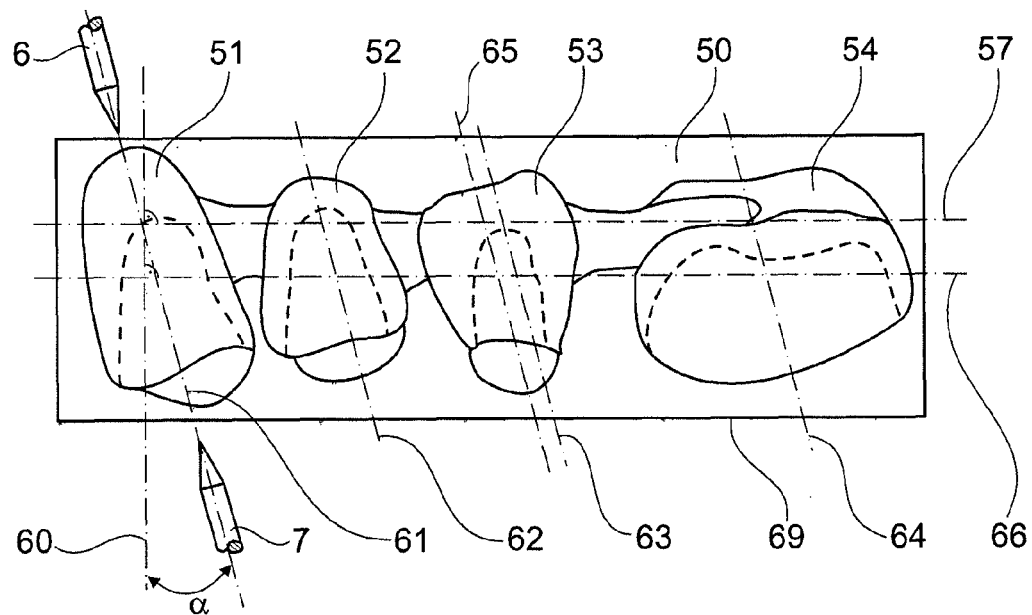
FIG. 5B shows the layout of a dental prosthetic item to be produced from a blank according to the invention.

FIGS. 5A, 5B show a dental prosthetic item 50 that is to be produced from a blank 49, 69 and comprises four members 51, 52, 53, 54.

In FIG. 5A, the dental prosthetic item 50 is disposed at an angle within the blank 49 as is customary in the prior art. That is to say, the central axis 56 of the blank 49 and the central axis 57 of the dental prosthetic item are inclined relatively to each other. This inclined arrangement is such that the machining tool 7' can produce the internal contour of the dental prosthetic item 50 along the machining axes 61 to 64. The machining axes 61 to 64 extend at right angles to the central axis 56 of the blank and at an angle to the central axis 57 of the dental prosthetic item 50, and they substantially coincide with an insertion axis 65 of the dental prosthetic item.

In FIG. 5b, the dental prosthetic item 50 is disposed in a blank 69 in such a way, according to the invention, that the insertion axis 65 of the dental prosthetic item 50 is inclined at an angle alpha in relation to the perpendicular 60 to the central axis 66 of the blank 69. The direction of the machining axes 61 to 64 corresponds to the insertion axis 65, and the machining tool 7 can produce an internal contour of the dental prosthetic item 50, at least partially, as indicated by dashed lines. After rotating the blank about the central axis 66, the remaining internal contour can be carved by means of the other machining tool 6.

In this case, the central axis 66 of the blank 69 and the central axis 57 of the dental prosthetic item 50 are approximately parallel to each other. Compared with the layout shown in FIG. 5a, this approximately parallel arrangement makes it possible to select a smaller blank 69. This has the advantage that the volume of the blank to be machined is reduced, as a result of which there are time advantages in the machining operation, and the service life of the grinding tools is improved. Furthermore, the use of a smaller blank is more economical than the use of a large one.

Figure 6:
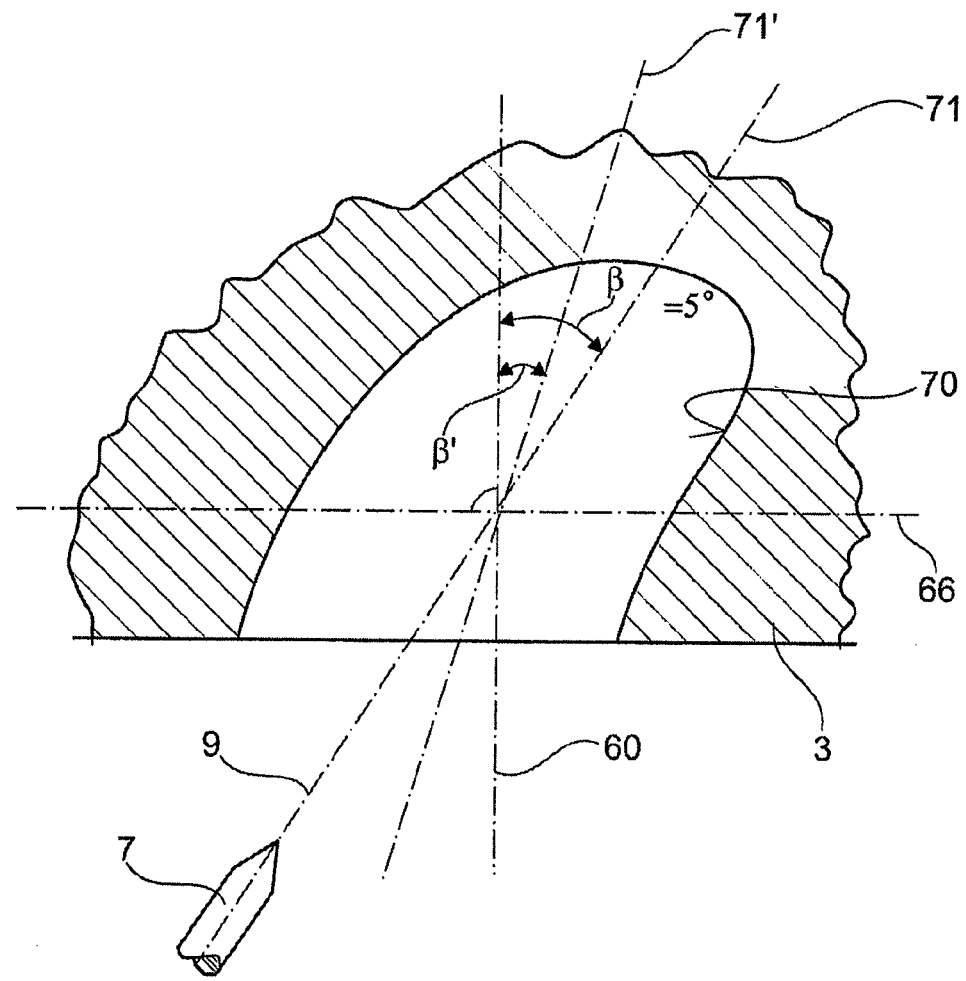
FIG. 6 shows an internal contour to be produced with an insertion axis that alters its degree of inclination as the depth of penetration increases.

FIG. 6 shows an internal contour 70 which is to be produced in the workpiece 3 and in which the insertion axis 71 alters its degree of inclination as the degree of penetration into the internal contour 70 increases. Starting from an angle of inclination of the insertion axis 71 relative to the perpendicular 60 to the central axis 66 of the workpiece 3 of 'beta' at the beginning of the internal contour, that is, at its open end, the degree of inclination of the insertion axis 71 changes to the angle beta at the end of the internal contour 70.

The angle beta of the insertion axis 71 can increase so as to be equal to the angle alpha of the feed axis 9 of the machining tool 7 relative to the perpendicular 60 to the central axis 66 of the workpiece 3.

Figure 7:
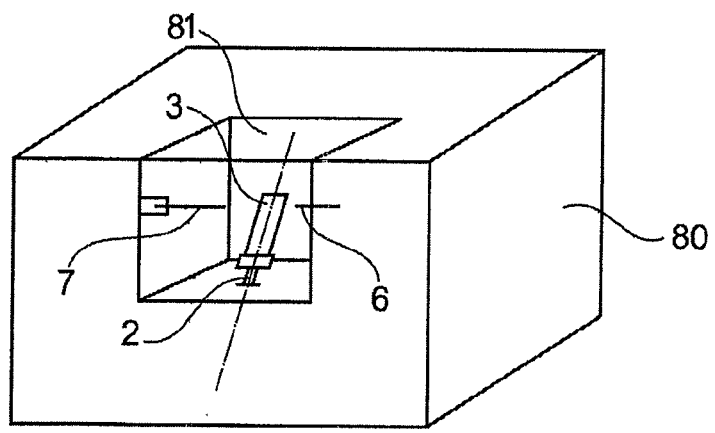
FIG. 7 shows a dental grinding machine according to the invention.

FIG. 7 shows a dental grinding machine 80 as an example of a machining device in which a workpiece 3 located on a workpiece holder 2 is arranged obliquely in a machining chamber 81 and can be machined from both sides by means of the machining tools 6, 7.

In general, the internal contour 70 can be carved completely whilst making optimal use of the blank as a result of the angular offset between the perpendicular 60 to the feed axis 4 of the workpiece 3 and the feed axis 9 of the machining tool 7 or, in reverse view, between the perpendicular 8', 9' to the feed axis 8, 9 of the tools 6, 7 and the workpiece axis 4. This also means that the available machining chamber 81 is better exploited without being larger and requiring longer machining tools and displacement paths.

The invention claimed is:

1. A machining device for a workpiece for the fabrication of dental prosthetic items or models thereof, comprising:
  a workpiece holder for said workpiece and a first and a second machining tool, wherein said workpiece holder on the one hand and said first and second machining tools on the other are capable of being moved relatively to each other along a first feed axis extending through said workpiece holder, and said first machining tool is disposed on a first side of said feed axis and said second machining tool is disposed on a side of said feed axis that opposes said first side, said first and second machining tools being capable of being moved relatively to said workpiece along a second feed axis extending through said machining tool and said workpiece is capable of being rotated through at least 180 degrees about said first feed axis, wherein said machine carries out machining of one side of said workpiece in a first position by one of said machining tools and then in a second position rotated through 180 degrees by the other machining tool, such machining being effected at an angle offset α of from 2 degrees to 15 degrees between said first feed axis and second feed axis of at least one of said two machining tools.

2. The machining device as defined in claim 1, wherein angular offset α of said two feed axes ranges from 3 to 10 degrees.

3. The machining device as defined in claim 1, wherein the perpendicular to the feed axis of at least one of said first and second machining tools is displaced in relation to said first feed axis by angular offset (α).

4. The machining device as defined in claim 1, wherein said workpiece holder is stationary along said first feed axis and that said machining tool is disposed on a guide and is capable of being moved relatively to said workpiece along said first feed axis.

5. A method for the fabrication of dental prosthetic items or models thereof by means of a first and a second machining tool, wherein a workpiece holder for said workpiece and said first and second machining tools are capable of being moved relatively to each other along a first feed axis extending through said workpiece holder, and said first machining tool is disposed on a first side of said feed axis and said second machining tool is disposed on a side of said feed axis that opposes said first side, and the first and second machining tools are capable of being moved relatively to said workpiece along a second feed axis extending through said machining tool, and said workpiece is capable of being rotated through at least 180 degrees about said first feed axis, and machining of one side of said workpiece is first carried out in a first position by one of said machining tools and then in a second position rotated through 180 degrees by the other machining tool, such machining being effected at an angle offset α of from 2 degrees to 15 degrees between said first feed axis and said second feed axis of at least one of said two machining tools.

6. The method as defined in claim 5, wherein said dental prosthetic item or model to be fabricated has at least one axis of insertion, wherein said dental prosthetic item or model to be fabricated is located within said workpiece such that the axis of insertion shows an angular offset (β) in relation to a perpendicular to a workpiece axis of from 2 to 15 degrees.

7. The method as defined in claim 6, wherein the arrangement is such that the angular offset beta of the axis of insertion is equal to not more than the angular offset (α) between said first feed axis and the perpendicular to said second feed axis of at least one of said two machining tools.

8. The machining device as defined in claim 2, wherein the perpendicular to the feed axial at least one of said first and second machining tools displaced in relation to said first feed axis by angular offset (α).

9. The machining device as defined in claim 2, wherein said workpiece holder is stationary along said first feed axis and that said machining tool is disposed on a guide and is capable of being moved relatively to said workpiece along said first feed axis.

10. The machining device as defined in claim 3, wherein said workpiece holder is stationary along said first feed axis and that said machining tool is disposed on a guide and is capable of being moved relatively to said workpiece along said first feed axis.

11. The machining device as defined in claim 8, wherein said workpiece holder is stationary along said first feed axis and that said machining tool is disposed on a guide and is capable of being moved relatively to said workpiece along said first feed axis.

12. The machining device as defined in claim 2, wherein said angular offset α ranges from 3.5 to 8 degrees.

13. The method as defined in claim 6, wherein said angular offset (β) ranges from 3.5 to 10 degrees.

\* \* \* \* \*